United States Patent [19]

Lewarchik et al.

[11] 4,228,294
[45] Oct. 14, 1980

[54] ESTERS OF IMIDAZOLIDINEDIONE-BASED DIEPOXIDES AND COATING COMPOSITIONS CONTAINING SAME

[75] Inventors: Ronald J. Lewarchik, Natrona Heights; J. Alden Erikson, Gibsonia; William J. Birkmeyer, Oakmont, all of Pa.

[73] Assignee: PPG Industries, Inc., Pittsburgh, Pa.

[21] Appl. No.: 950,105

[22] Filed: Oct. 10, 1978

[51] Int. Cl. .............................................. C07d 233/72
[52] U.S. Cl. .................................. 548/312; 526/263; 528/73; 528/367
[58] Field of Search ............... 548/310, 312; 526/263; 528/73, 367, 407, 418

[56] References Cited

U.S. PATENT DOCUMENTS

| | | | |
|---|---|---|---|
| 3,629,263 | 12/1971 | Batzer | 548/312 |
| 3,631,221 | 12/1971 | Batzer | 548/312 |
| 3,808,226 | 4/1974 | Habermeier | 548/312 |
| 3,813,352 | 5/1974 | Habermeier | 260/2 EP |
| 3,828,045 | 8/1974 | Batzer | 260/260 |
| 3,852,302 | 12/1974 | Habermeier | 548/312 |
| 3,904,644 | 9/1975 | Jaeger | 260/309.5 |
| 4,137,139 | 1/1979 | Seltzer | 548/312 |
| 4,150,234 | 4/1979 | Seltzer | 548/312 |

Primary Examiner—Paul R. Michl
Attorney, Agent, or Firm—Charles R. Wilson

[57] ABSTRACT

Esters of imidazolidinedione-based diepoxides are especially useful in coating compositions having a low organic solvent content. The esters have the structure

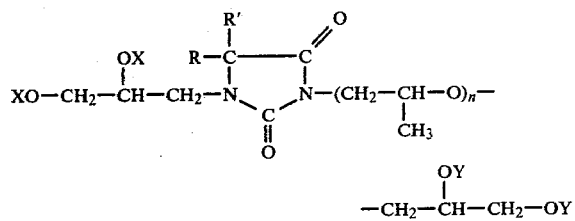

wherein R and R' are independently hydrogen or hydrocarbon groups having from 1 to 8 carbon atoms, one X is hydrogen and the other X is

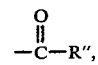

one Y is hydrogen and the other Y is

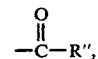

where the R" groups are independently saturated hydrocarbon groups having from 1 to 17 carbon atoms or unsaturated hydrocarbon groups having from 4 to 17 carbon atoms and n is 0 or 1.

27 Claims, No Drawings

ESTERS OF IMIDAZOLIDINEDIONE-BASED DIEPOXIDES AND COATING COMPOSITIONS CONTAINING SAME

BACKGROUND OF THE INVENTION

The subject invention relates to novel esters and coating compositions containing them. More particularly, it relates to esters of imidazolidinedione-based diepoxides and their use in coating compositions.

There have been recent concerns as to the polluting effects and health concerns associated with the use of organic solvents. Many useful coating compositions contain appreciable amounts of organic solvents. Precautions in the use of the coating compositions and the installation of solvent recovery systems have alleviated some of the concerns. However, it would still be desirable to formulate coating compositions containing little or no organic solvent.

Various attempts have been made to lower the organic solvent content in coating compositions. One line of work has concentrated on using water as the liquid carrier in place of the organic solvent. However, this has necessitated changes in the resin formulations with a consequent change in performance obtained from the coating compositions.

Another line of work has attempted to formulate coating compositions containing a high solids content, and thus low organic solvent content. The problem associated with many of the high solids coating compositions has been the fact such compositions normally are highly viscous and are hard to apply using conventional coating techniques. The formulation of coating compositions having a low organic solvent content which also possess a viscosity which allows the composition to be applied by conventional techniques would be most desirable.

There have now been found novel compounds which when properly formulated into coating compositions provide compositions which can be readily applied and give coatings having a desired set of properties.

As used herein, all percents and ratios are by weight unless otherwise indicated.

SUMMARY OF THE INVENTION

The ester described herein have the formula:

$$\text{XO}-\text{CH}_2-\overset{\text{OX}}{\underset{|}{\text{CH}}}-\text{CH}_2-\text{N} \overset{R-\overset{R'}{\underset{|}{C}}-\overset{\nearrow O}{C}}{\underset{\underset{O}{\overset{\|}{C}}}{}} \text{N}-(\text{CH}_2-\overset{|}{\underset{\text{CH}_3}{\text{CH}}}-\text{O})_n-$$

$$-\text{CH}_2-\overset{\text{OY}}{\underset{|}{\text{CH}}}-\text{CH}_2-\text{OY}$$

wherein R and R' are independently hydrogen or hydrocarbon groups having from 1 to 8 carbon atoms, one X is hydrogen and the other X is $$-\overset{O}{\underset{\|}{C}}-R'',$$

one Y is hydrogen and the other Y is $$-\overset{O}{\underset{\|}{C}}-R'',$$

where the R'' groups are independently saturated hydrocarbon groups having from 1 to 17 carbon atoms or unsaturated hydrocarbon groups having from 4 to 17 carbon atoms and n is 0 or 1.

The above esters of imidazolidinedione-based diepoxides are especially useful when formulated with a crosslinking agent selected from the group consisting of aminoplasts, isocyanates, blocked isocyanates, phenoplasts, beta-hydroxyalkylamines and mixtures thereof to form a coating composition. The coating compositions can have an organic solvent content of below about 40 percent.

DETAILED DESCRIPTION OF THE INVENTION

The following paragraphs describe the esters of imidazolidinedione-based diepoxides, their process of making and their use in coating compositions.

Esters of imidazolidinedione-based diepoxides of this invention have the formula:

$$\text{XO}-\text{CH}_2-\overset{\text{OX}}{\underset{|}{\text{CH}}}-\text{CH}_2-\text{N} \overset{R-\overset{R'}{\underset{|}{C}}-\overset{\nearrow O}{C}}{\underset{\underset{O}{\overset{\|}{C}}}{}} \text{N}-(\text{CH}_2-\overset{|}{\underset{\text{CH}_3}{\text{CH}}}-\text{O})_n-$$

$$-\text{CH}_2-\overset{\text{OY}}{\underset{|}{\text{CH}}}-\text{CH}_2-\text{OY}$$

wherein R and R' are independently hydrogen or hydrocarbon groups having from 1 to 8 carbon atoms, one X is hydrogen and the other X is $$-\overset{O}{\underset{\|}{C}}-R'',$$

one Y is hydrogen and the other Y is $$-\overset{O}{\underset{\|}{C}}-R'',$$

where the R'' groups are independently saturated hydrocarbon groups having from 1 to 17 carbon atoms or unsaturated hydrocarbon groups having from 4 to 17 carbon atoms and n is 0 or 1.

The above-described esters where n is 0 are made from diepoxides of the formula $$\overset{O}{\underset{\diagup \diagdown}{\text{CH}_2-\text{CH}}}-\text{CH}_2-\text{N} \overset{R-\overset{R'}{\underset{|}{C}}-\overset{\nearrow O}{C}}{\underset{\underset{O}{\overset{\|}{C}}}{}} \text{N}-\text{CH}_2-\overset{O}{\underset{\diagup \diagdown}{\text{CH}-\text{CH}_2}}.$$

These diepoxides are available commercially or can be manufactured from the reaction product of N-heterocyclic compounds having the formula

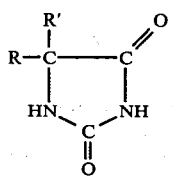

and an epihalohydrin. R and R' represent hydrogen groups, alkyl groups or, when joined, a cycloalkyl group. (It should be understood that the R and R' groups can be the same or different.) Preferably, R and R' are alkyl groups having from 1 to 5 carbon atoms. Examples of N-heterocyclic compounds are 2,4-imidiazolidinedione (more commonly referred to as hydantoin), 5-methyl-2,4-imidazolidinedione, 5,5-dimethyl-2,4-imidazolidinedione, 5-methyl-5-ethyl-2,4-imidazolidinedione, 5-ethyl-5-amyl-2,4-imidazolidinedione, 5-propyl-2,4-imidazolidinedione, 5-isopropyl-2,4-imidazolidinedione and 5,5-pentamethylene-2,4-imidazolidinedione. Suitable epihalohydrins include epichlorohydrin and epibromohydrin.

Suitable catalysts for use in the reaction of the imidazolidinedione with the epihalohydrin are tertiary amines such as triethylamine, tri-n-propylamine, benzyldimethylamine, N,N-dimethylaniline and triethanolamine, quaternary ammonium hydroxide, quaternary ammonium halides, alkali halides such as lithium chloride, potassium chloride and sodium chloride, and hydrazines with a tertiary nitrogen atom. As a general rule, the reaction of the imidazolidinedione with epihalohydrin occurs at elevated temperatures, e.g., from about 60° C. to about 200° C. Agents for splitting off hydrogen halide which are used are, as a rule, strong alkalis such as anhydrous sodium hydroxide or concentrated sodium hydroxide solution. However, other alkaline reagents such as potassium hydroxide, barium hydroxide, sodium carbonate or potassium carbonate can also be used to produce the diepoxides.

The diepoxides used in this invention wherein n is 1 have the formula

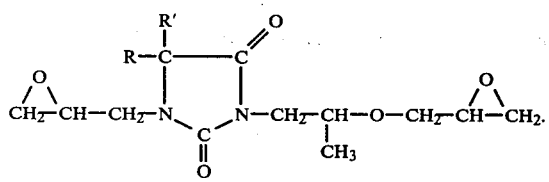

These diepoxides are available commercially or can be derived from compounds of the general formula:

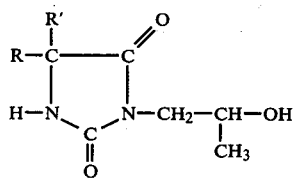

wherein R and R' are as above defined. Such compounds are described in U.S. Pat. No. 3,828,045, the disclosure of which is herein incorporated by reference. These imidazolidinediones are initially reacted with an epihalohydrin in a known manner. For instance, in a single stage process, the reaction of the imidazolidinedione with the epihalohydrin takes place in the presence of an alkali such as sodium hydroxide or potassium hydroxide. Alternatively, the imidazolidinedione can be condensed in a first stage with an epihalohydrin in the presence of acids or basic catalysts such as tetraethyl ammonium chloride to give the halohydrin compound. Thereafter the latter is dehydrohalogenated in a second stage by means of alkalis such as potassium hydroxide or sodium hydroxide to give the diepoxide.

Esters of the above described diepoxides where n is 0 or 1 are made by the reaction of the diglycidyl compound with a carboxylic acid. Such carboxylic acids can be saturated or unsaturated, aliphatic or cyclic compounds. The saturated aliphatic carboxylic acids have from 2 to 18 carbon atoms. Cyclic carboxylic acids used in the reaction are aryl and alkylaryl compounds having from 7 to 11 carbon atoms, i.e. 6 to 10 carbon atoms exclusive of the carbon atom in the carboxyl group. Examples of such acids include acetic acid, propionic acid, butyric acid, caproic acid, myristic acid, palmitic acid, stearic acid, neodecanoic acid, dodecanoic acid, pelargonic acid, benzoic acid, toluic acid, phenylacetic acid, oxalic acid, malonic acid, succinic acid, glutaric acid, adipic acid, octanedioic acid, azelaic acid, sebacic acid, phthalic acid, isophthalic acid, terephthalic acid, hexahydrophthalic acid and the anhydrides where they exist. Unsaturated carboxylic acids can also be used. Such acids contain from 5 to 18 carbon atoms, examples of which are myristoleic acid, palmitoleic acid, oleic acid, linoleic acid and linolenic acid. The monocarboxylic acids are preferred with the saturated monocarboxylic acids having from 8 to 18 carbon atoms being most preferred. A particularly preferred saturated carboxylic acid is neodecanoic acid.

The formation of the ester occurs at a temperature of from about 50° C. to about 200° C. A suitable catalyst such as a tertiary amine, quaternary ammonium hydroxide, quarternary ammonium halide or lithium carbonate can be used.

The above-described esters have a relatively low molecular weight, yet are substantially non-volatile upon exposure to elevated temperatures. The esters can also be thinned with relatively little organic solvent to substantially reduce their viscosities. These properties make the esters especially useful in coating compositions where only a low level of organic solvent can be tolerated. Thus coating compositions can be formulated with the esters and suitable crosslinking agents using little or no organic solvent. The resultant composition have a low viscosity and can be applied using conventional coating techniques. Moreover, coatings resulting from the compositions are durable, have a good appearance and can have a high gloss.

COATING COMPOSITIONS

Coating compositions of this invention consist essentially of from about 5 percent to about 90 percent of the above ester of imidazolidinedione-based-diepoxide, preferably from about 10 percent to about 50 percent of the ester, and from about 5 percent to about 80 percent, preferably from about 20 percent to about 60 percent, of a suitable crosslinking agent. Examples of crosslinking agents are the aminoplasts, isocyanates, blocked isocyanates, phenoplasts and beta-hydroxyalkylamides and mixtures thereof. Preferred are the aminoplasts and blocked isocyanates. The aforedescribed classes of crosslinking agents are described in more detail in the following paragraphs.

Aminoplast resins are based on the addition products of formaldehyde, with an amino- or amido-group carrying substance, e.g., urea, ethylene diurea, ethylene urea, melamine and benzoguanamine. Condensation products obtained from the reaction of alcohols and formaldehyde with melamine, urea or benzoguanamine are preferred herein. Useful alcohols used to make etherified products are monohydric alcohols such as methanol, ethanol, propanol, butanol, benzyl alcohol and butoxyethanol. An etherified melamineformaldehyde resin is the preferred aminoplast resin. U.S. Pat. No. 4,075,141, Porter et al, Feb. 21, 1978, contains a description of useful aminoplast resins and is incorporated herein by reference.

Isocyanates useful as a crosslinking agent include any of the many organic isocyanates available. Examples include p-phenylene diisocyanate, biphenyl diisocyanate, toluene diisocyanate, 3,3'-dimethyl-4,4'-biphenylene diisocyanate, 1,4-tetramethylene diisocyanate, hexamethylene diisocyanate, 2,2,4-trimethylhexane-1,6-diisocyanate, methylene bis(phenylisocyanate), isophorone diisocyanate, 1,2,4-benzene triisocyanate, polymethylene polyphenyl isocyanate, bis(isocyanatocyclohexyl)methane and methyl cyclohexyl diisocyanate, as well as derivatives thereof.

Blocked isocyanates containing substantially no free isocyanate groups and relatively inactive at room temperature are very useful crosslinking agents. Typical blocking agents are the phenols, thiols, oximes, caprolactams, and secondary aromatic amines. Many of these compounds are commercially available. "The Chemistry of Organic Film Formers", Robert E. Krieger Pub. Co., copyrighted 1977, by D. H. Solomon, pp. 216–217, contains a description of many blocked isocyanates that can be used here. This disclosure is herein incorporated by reference.

Phenoplast resins include the condensation product of an aldehyde with a phenol. Formaldehyde is a preferred aldehyde. Various phenols can be used, e.g., phenol per se, cresol, para-phenylphenol, para-tertiarybutyl-phenol, para-tertiaryamylphenol and cyclopentylphenol. The methylol phenol ethers described in U.S. Pat. No. 2,597,330 (herein incorporated by reference) are especially useful.

Another type of useful crosslinking agents are the beta-hydroxyalkylamides. These crosslinking agents are described in "Journal of Coatings Technology", *Beta-Hydroxyalkylamides, Low Polluting Crosslinkers For Carboxyl Containing Polymers*, Vol. 50, No. 643, August 1978 (the disclosure of which is hereby incorporated by reference). Specific examples of such compounds are N-methyl-N-(beta-hydroxyethyl)-4-pentenamide and bis[N,N-di(beta-hydroxypropyl)]adipamide.

The coating compositions consist essentially of the aforedescribed esters of imidazolidinedione-based diepoxides and the crosslinking agents. Generally, however, coating composition additives are included in the compositions. A solvent such as water or an organic solvent, e.g., the ketones, ethylene glycol monoalkyl ether acetates, the mono- and dialkyl ethers of ethylene and propylene glycol, xylene, toluene and lower alcohols can be used. The level of the organic solvent in the composition, however, is less than about 40 percent, preferably less than about 30 percent, of the composition. Other coating composition additives include pigments, fillers, antioxidants, flow control agents, surfactants, catalysts and reactive diluents. Other curable resins can also be included in the compositions provided they do not exceed about 60 percent of the coating composition.

The coating compositions are applied by any convenient method, including spraying, dipping and flow coating. The compositions have been found especially useful for the coating of metal substrates such as automotive parts.

The following examples are illustrative of the described invention, with Example V representing a preferred embodiment. The exemplified processes all produce the esters of imidazolidinedione-based diepoxides of this invention.

EXAMPLE I

A three-liter reaction flask is equipped with heating means and stirring means. The flask is initially charged with 1,000 grams of imidazolidinedione-based diepoxides, available from the Ciba-Geigy Co. as XB-2793, 1,098 grams of pelargonic acid and 6.3 grams dimethyl-coco-amine. The imidazolidinedione-based diepoxides are a mixture of 70 percent, 5,5-dimethyl-1,3-diglycidyl-2,4-imidazolidinedione, and 30 percent 5,5-dimethyl-1-glycidyloxypropyl-2,4-imidazolidinedione. The reaction mixture is heated to 120° C. and allowed to exotherm to about 140° C. The mixture is kept at 140° C. for about 5 hours until an acid number below 1 is obtained. The resultant mixture has a Gardner-Holdt viscosity of Z-3 and a hydroxyl number of 189.4.

EXAMPLE II

A five-liter reaction flask is set up as in Example I. To the flask is charged 1,253 grams of imidazolidinedione-based diepoxides, available from the Ciba-Geigy Co. as XB-2793, 1,217 grams of tall oil fatty acids, 530 grams of benzoic acid and 9 grams of dimethyl-coco-amine.

The reactants are heated to 100° C. and allowed to exotherm to 140° C. while maintaining a nitrogen blanket. The reaction mixture is held at 140° C. for about 4½ hours until an acid number of below 1 is obtained.

The above reaction mixture has a Gardner-Holdt viscosity of Z-8, an acid number of 0.76 and a hydroxyl number of 195.

EXAMPLE III

A five-liter reaction flask set up as in Example I is charged with 1,352 grams of the imidazolidinedione-based diepoxides used in Example I, 1,648 grams of Versatic 911 Acid (a saturated synthetic tertiary monocarboxyl acid having 9–11 carbon atoms and made by Shell Chemical Co.) and 9 grams of dimethyl-coco-amine. The reaction mixture is heated to 100° C. and allowed to exotherm to about 140° C. The mixture is held at this temperature for about 8 hours, until an acid number of below 1 is obtained.

The resultant reaction mixture has a Gardner-Holdt viscosity of Z-8, an acid number of 4.1 and a solids content of 98.6 percent.

EXAMPLE IV

To a five-liter reaction flask set up as in Example I is charged 1,500 grams of 5-ethyl-5-amyl-1,3-diglycidyl-2,4-imidazolidinedione (available from the Ciba-Geigy Co. as LSU-609), 1,500 grams of pelargonic acid and 9 grams of dimethyl-coco-amine. The mixture is heated to 100° C. and allowed to exotherm to 140° C. The mixture is held at this temperature until an acid number of below about 1 is obtained. This occurs after about 9 hours.

The mixture has a Gardner-Holdt viscosity of Z-2, an acid number of 1.5 and a hydroxyl value of 184.

EXAMPLE V

A five-liter reaction flask is charged with 1,432 grams of the imidazolidinedione-based diepoxide of Example IV, 1,568 grams of neodecanoic acid and 9 grams of dimethyl-coco-amine. The mixture is heated to 100° C. and allowed to exotherm to about 140° C. The mixture is held at this temperature for 4 hours, until an acid number of below 1 is obtained.

The reaction mixture has a viscosity of Z-7, an acid number of 0.4 and a hydroxyl number of 188.

EXAMPLE VI

Following the procedure of Example I, a five-liter reaction flask is charged with 1,490 grams of 5,5-pentamethylene-1,3-diglycidyl-2,4-imidazolidinedione (available from the Ciba-Geigy Co. as LSU-549), 1,510 grams pelargonic acid and 9 grams dimethyl-coco-amine. The mixture is allowed to exotherm to 140° C. and is maintained at that temperature for about 4½ hours until an acid number of below 1 is obtained.

The reaction mixture has a viscosity of Z-6, an acid number of 0.4 and a hydroxyl value of 200.

EXAMPLE VII

A five-liter reaction flask equipped as in Example I is charged with 1262 grams of the imidazolidinedione-based diepoxides of Example I, 1312 grams of pelargonic acid, 426 grams hexahydrophthalic anhydride and 9 grams dimethyl-coco-amine. The reaction mixture is heated to 140° C. and maintained at that temperature until an acid number of below 50 is obtained. The reaction requires about 1 hour.

The resultant reaction mixture after being thinned to 90 percent theoretical solids with ethylene glycol monoethyl ether acetate has an acid number of 41.0, hydroxyl number of 103.5 and a Gardner-Holdt viscosity of Z-4.

EXAMPLE VIII

A coating composition is formulated as follows:

|  | Percent |
| --- | --- |
| Ester of Example V | 24.3 |
| Methylated melamine-formaldehyde condensate (1) | 21.3 |
| Microgel dispersion (2) | 9.2 |
| Pigment paste (3) | 39.2 |
| Para-toluenesulfonic acid | 1.3 |
| Diisopropanolamine | 0.2 |
| Ethanol | 4.5 |

(1) The methylated melamine-formaldehyde condensate is an aminoplast resin sold by American Cyanamid Co. as Cymel 303.
(2) The microgel dispersion corresponds to the dispersion described in Example II of commonly assigned copending application S.N. 805,679, filed June 13, 1977.
(3) The pigment paste contains 67 percent titanium dioxide; 12 percent of a pigment grind resin based on 10% hydroxyethyl acrylate, 4 percent methacrylic acid, 20 percent styrene, 15 percent 2-ethylhexyl acrylate and 51 percent isobutyl methacrylate and; 21 percent of a solvent blend of ethylene glycol monoethyl ether acetate, butanol and methyl ethyl ketone.

The above composition has an 81.2 percent solids content and a viscosity of 31 poises.

The composition is readily applied by spray means to a metal panel. The coated panel, after being baked at 120° C. for 30 minutes, has an acceptable appearance and compares favorably with a commercially used enamel in terms of its sag resistance, solvent resistance, acid resistance and water soak resistance.

EXAMPLE IX

A coating composition using an isocyanate as a crosslinking agent is formulated as follows:

|  | Percent |
| --- | --- |
| Ester of Example I | 18.0 |
| Isocyanate (1) | 50.0 |
| Dibutyltin dilaurate | 0.6 |
| Pigment paste (2) | 7.5 |
| Ethylene glycol monoethyl ether acetate | 14.2 |
| Acetone | 9.7 |

(1) The isocyanate is an isophorone diisocyanate-based isocyanurate-containing adduct made by Veba-Chemie AG as T-1890.
(2) The pigment paste contains 46.2 percent aluminum pigment; 25.0 percent of a grind resin made from 10 percent hydroxyethyl acrylate, 2.5 percent methacrylic acid (with 25 percent of the methacrylic acid reacted with hydroxyethylethyleneimine), 30 percent styrene, 20 percent 2-ethylhexyl acrylate, 19.5 percent butyl methacrylate and 18 percent methyl methacrylate; and 28.8 percent solvent.

The above composition is sprayed at a level sufficient to give a 2.0 mil dry film on a metal panel when baked at 80° C. for 25 minutes. The coated panel is found to have good sag resistance, solvent resistance, water soak resistance, adhesion and appearance.

EXAMPLE X

A preferred formulation found to give a coated panel especially good characteristics is as follows:

|  | Percent |
| --- | --- |
| Ester of Example V | 5.4 |
| Aminoplast resin (1) | 19.2 |
| Acrylic resin | 7.7 |
| Pigment paste (2) | 41.3 |
| Microgel Dispersion (3) | 13.9 |
| Methyl ethyl ketone | 2.1 |
| Ethanol | 5.6 |
| Para-toluenesulfonic acid | 1.7 |
| Diisopropanolamine | 1.1 |
| Cellulose acetate butyrate (4) | 2.0 |

(1) A melamine resin available from Monsanto Co. as Resimene 755.
(2) The pigment paste of Example VIII.
(3) The microgel dispersion of Example VIII.
(4) The cellulose acetate butyrate is available from Eastman Kodak Co. as CAB 551.2.

The above composition has a solids content of 72.0 percent. The composition provides a durable coating to metal panels when applied as a spray and tested as in Example VIII.

The above examples illustrate the making of the esters of this invention and their use in coating compositions. Coated substrates based on the coating compositions all possess durable finishes with satisfactory appearances.

What is claimed is:

1. An ester of imidazolidinedione-based diepoxide having the structure:

$$XO-CH_2-CH(OX)-CH_2-N\underset{\underset{O}{\|}}{\overset{}{\underset{C}{\diagdown}}}\overset{R'}{\underset{\diagup}{\overset{|}{\underset{|}{C}}-\overset{O}{\underset{}{\overset{\diagup\!\!\diagup}{C}}}}}N-(CH_2-CH(CH_3)-O)_n-$$

-continued

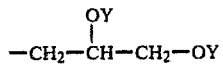

wherein R and R' are independently hydrogen or hydrocarbon groups having from 1 to 8 carbon atoms, one X is hydrogen and the other X is

one Y is hydrogen and the other Y is

where the R" groups are independently (a) alkyl groups having from 1 to 17 carbon atoms or (b) aryl or alkylaryl groups having from 6 to 10 carbon atoms and n is 0 or 1.

2. The ester of claim 1 wherein R and R' are hydrogens.

3. The ester of claim 1 wherein R and R' are alkyl groups.

4. The ester of claim 3 wherein the alkyl groups have from 1 to 5 carbon atoms.

5. The ester of claim 4 wherein R and R' are joined to form a cycloalkyl group.

6. The ester of claim 1 wherein R is hydrogen and R' is an alkyl group.

7. The ester of claim 2, 3 or 6 wherein the R" groups are alkyl groups.

8. The ester of claim 7 wherein the R" alkyl groups have from 7 to 17 carbon atoms.

9. The ester of claim 8 wherein the alkyl groups are tertiary alkyl groups.

10. The ester of claims 2, 3 or 6 wherein the R" groups are aryl or alkylaryl groups having from 6 to 10 carbon atoms.

11. The ester of claims 2, 3 or 6 wherein n is 0.

12. The ester of claims 2, 3 or 6 wherein n is 1.

13. A coating composition containing less than about 40 percent organic solvent, consisting essentially of:
(a) from about 5 percent to about 90 percent of an ester of imidazolidinedione-based diepoxide having the structure:

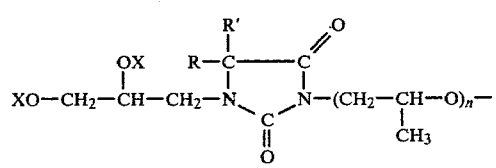

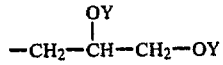

wherein R and R' are independently hydrogen or hydrocarbon groups having from 1 to 8 carbon atoms, one X is hydrogen and the other X is

one Y is hydrogen and the other Y is

where the R" groups are independently (a) alkyl groups having from 1 to 17 carbon atoms or (b) aryl or alkylaryl groups having from 6 to 10 carbon atoms and n is 0 or 1; and
(b) from about 5 percent to about 80 percent of a crosslinking agent selected from the group consisting of aminoplasts, isocyanates, blocked isocyanates, phenoplasts, beta-hydroxyalkylamides and mixtures thereof.

14. The composition of claim 13 wherein the composition contains less than about 30 percent organic solvent.

15. The composition of claim 13 wherein R and R' are hydrogens.

16. The composition of claim 13 wherein R and R' are alkyl groups.

17. The composition of claim 16 wherein the alkyl groups have from 1 to 5 carbon atoms.

18. The composition of claim 17 wherein the alkyl groups are joined to form a cycloalkyl group.

19. The composition of claim 13 wherein R is hydrogen and R' is an alkyl group.

20. The composition of claim 15, 16 or 19 wherein the R" groups are alkyl groups.

21. The composition of claim 20 wherein the R" alkyl groups have from 7 to 17 carbon atoms.

22. The composition of claims 15, 16 or 19 wherein the R" groups are aryl or alkylaryl groups having from 6 to 10 carbon atoms.

23. The composition of claims 15, 16 or 19 wherein n is 0.

24. The composition of claims 15, 16 or 19 wherein n is 1.

25. The composition of claim 13 wherein the crosslinking agent is an aminoplast.

26. The composition of claim 13 wherein the crosslinking agent is a blocked isocyanate.

27. The composition of claims 13, 25 or 26 wherein the ester represents from about 10 percent to 50 percent of the composition and the crosslinking agent from about 20 percent to about 60 percent of the composition.

* * * * *